(12) United States Patent
Schickaneder et al.

(10) Patent No.: US 6,469,213 B1
(45) Date of Patent: Oct. 22, 2002

(54) TRAMADOL, SALTS THEREOF AND PROCESS FOR THEIR PREPARATION

(75) Inventors: Helmut Schickaneder; Aggelos Nikolopoulos, both of Cork (IE)

(73) Assignee: Russinsky Limited, Cork (IE)

( * ) Notice: Subject to any disclaimer, the term of this patent is extended or adjusted under 35 U.S.C. 154(b) by 0 days.

(21) Appl. No.: 09/482,889

(22) Filed: Jan. 14, 2000

Related U.S. Application Data

(63) Continuation of application No. PCT/IE98/00051, filed on Jun. 26, 1998.

(30) Foreign Application Priority Data

Jul. 15, 1997 (IE) .................................................. 970519

(51) Int. Cl.$^7$ ............................................ C07C 209/00
(52) U.S. Cl. ........................ 564/425; 564/304; 564/438; 564/443
(58) Field of Search ................................ 564/304, 425, 564/438, 443

(56) References Cited

U.S. PATENT DOCUMENTS

| | | | |
|---|---|---|---|
| 3,652,589 A | 3/1972 | Flick et al. | 260/326.5 |
| 5,223,541 A | 6/1993 | Maryanoff et al. | 514/644 |
| 5,336,691 A | 8/1994 | Raffa et al. | 514/629 |
| 5,414,129 A | 5/1995 | Cherkez et al. | 564/425 |
| 5,516,803 A | 5/1996 | Raffa | 514/570 |

FOREIGN PATENT DOCUMENTS

| | | |
|---|---|---|
| EP | 0534628 | 3/1993 |
| EP | 0778262 | 6/1997 |
| EP | 0787715 | 8/1997 |
| EP | 0831082 | 3/1998 |
| GB | 997399 | 7/1965 |

OTHER PUBLICATIONS

Raffa et al, Journal of Pharacology . . . , vol. 267, No. 1, 1993, "Complementary and Synergistic . . . ", pp. 331–342.

Chemical Abstracts, vol. 126, No. 26, Jun. 30, 1997, & IL 1030 096 A (Chemagis Ltd), Dec. 5, 1996.

Chemical Abstracts, vol. 127, No. 20, Nov. 17, 1997, Ben–Zhi et al, "Synthesis and structure of . . . ".

*Primary Examiner*—Samuel Barts
(74) *Attorney, Agent, or Firm*—Jacobson Holman, PLLC

(57) ABSTRACT

Cis-Tramadol hydrochloride is prepared by forming a Mannich hydrochloride, liberating the Mannich base, reacting the Mannich base with a Grignard reagent to form a base hydrate of cis-Tramadol which is used to form pure cis-Tramadol hydrochloride. Also claimed is the base hydrate of cis-Tramadol per se and its use as a medicament.

12 Claims, 2 Drawing Sheets

TRAMADOL, SALTS THEREOF AND PROCESS FOR THEIR PREPARATION

Figure 1:
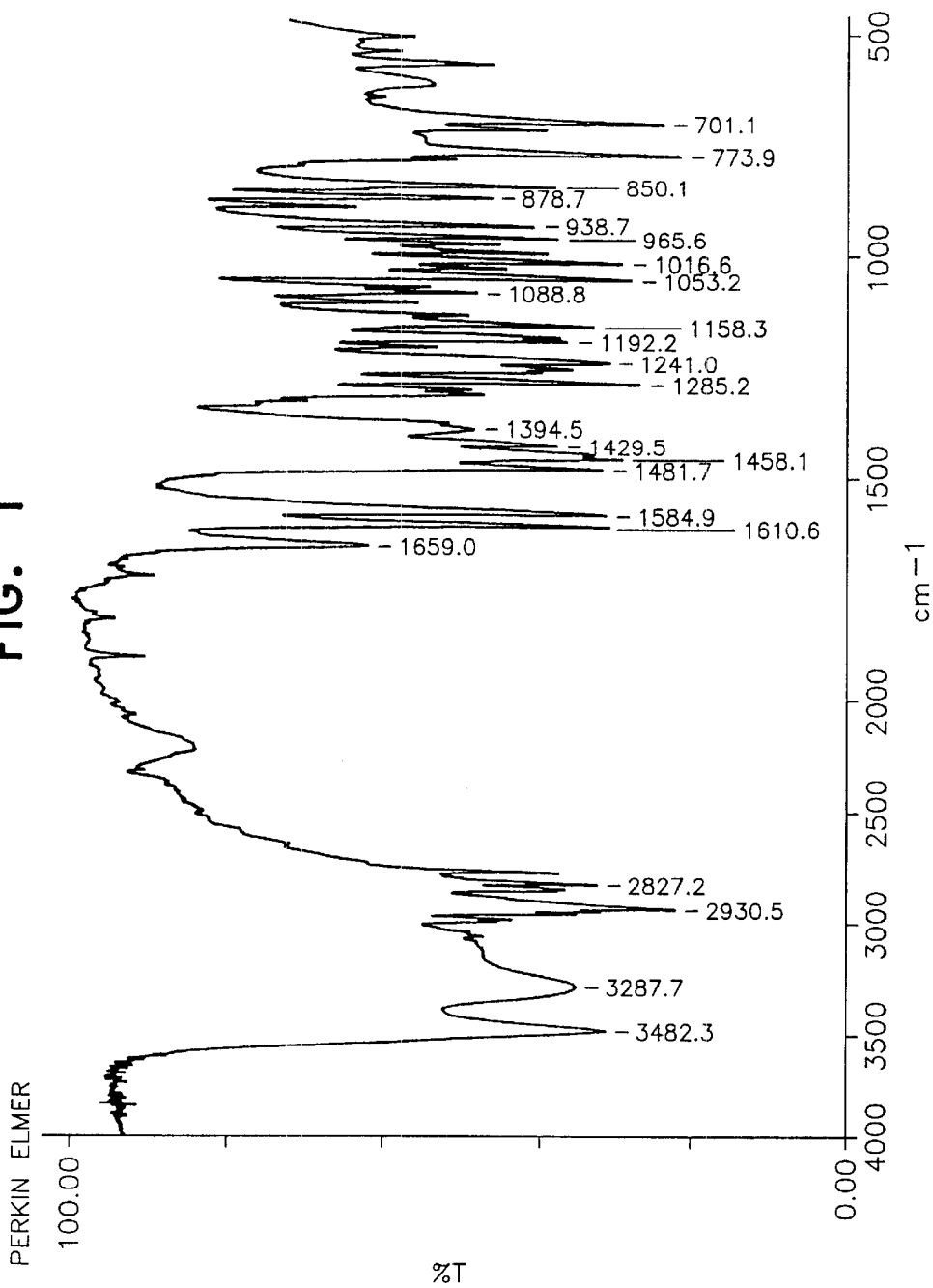

This application is a continuation of PCT/IE98/00051 filed Jun. 26, 1998.

The invention relates to a new, stable and pure Tramadol derivative, a specific process for preparing it and its use. The invention also relates to a process for producing Tramadol and salts thereof, especially Tramadol hydrochloride using the derivative.

Tramadol is the compound cis(+/−)-2-[(dimethylamino)-methyl]-1-(3-methoxyphenyl) cyclohexanol which, in the form of the hydrochloride salt is widely used as an analgesic.

Tramadol hydrochloride assumes a special position among centrally acting ;s analgesics since this active ingredient acts as a strong inhibitor of pain without the side effects which are known for opioids (T. Phannacol. Exptl. Ther. 267,331 (1993)).

The compound per se is described in U.S. Pat. No. 3,652,589 and UK 997,399. Tramadol is obtained in the cis-racemate form as the major synthetic product. In known processes, the trans-racemate is present as a minor component of the reaction mixture. U.S. Pat. No. 3,652,589 describes an isolation process for the pure cis-racemate-isomer in which a complex Grignard reaction mixture is distilled and the crude mixture of the isomers is precipitated and filtered. However, there is still a relatively high level of the trans-racemate-isomer present in the final product.

U.S. Pat. No. 5,414,129 describes a process for the purification and separation of cis(+/−)-2-[(dimethylamino) methyl]-1-(3-methoxyphenyl) cyclohexanol-hydrochloride from a reaction mixture containing the cis-racemate-isomer, the trans-racemate-isomer and Grignard reaction side products In that process, the reaction mixture is combined with a solution of hydrochloric acid in a $C_2$–$C_3$ alcohol or with gaseous hydrogen chloride in the presence of specific solvents. The process is said to effect the selective precipitation of cis(+/−)-2-[(dimethylamino)methyl]-1-(3-methoxyphenyl) cyclohexanol-hydrochloride. A specific example using isopranol is given and the process is also said to have been successful using one of the following solvents as an alternative: butyl acetate, MIBK, 1-butanol, 1-pentanol,PAA (primary amyl alcohol mixture), 1-hexanol, cyclohexanol, 1-octanol, 2-ethylhexanol, anisole.

However, the yield of the cis(+/−)-isomer is still relatively low and the content of the trans(+/−)-isomer is relatively high in most cases.

There is therefore a need for an improved process for preparing the pure cis form of Tramadol without several further purification steps.

Tramadol can exist in either its cis or trans isomer forms. In this specification cis-Tramadol means the racemic mixture of cis-Tramadol as shown by the following chemical structures:

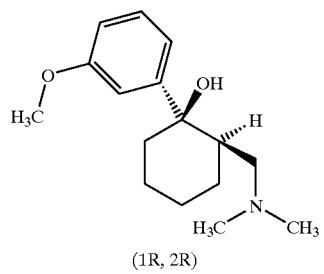
(1R, 2R)

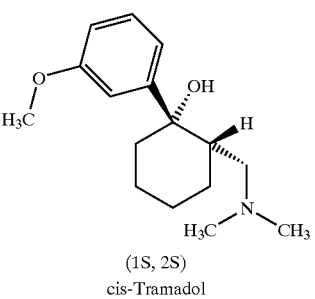
(1S, 2S)
cis-Tramadol

STATEMENTS OF INVENTION

According to the invention, there is provided the base hydrate of cis-Tramadol as herein defined.

The invention also provides the use of the base hydrate of cis-Tramadol as an intermediate in a process for preparing Tramadol Hydrochloride.

The invention further provides the use of the base hydrate of cis-Tramadol as a medicament.

In addition, the invention provides a pharmaceutical composition including the base hydrate of cis-Tramadol. The composition may be in a form for oral, buccal, topical and parenteral or of rectal administration, especially parenteral administration.

In another aspect, the invention provides a process for preparing pure cis-Tramadol hydrochloride comprising the steps of:

reacting a Mannich base with a Grignard reagent to form a base hydrate of cis-Tramadol; and forming cis-Tramadol hydrochloride from the base hydrate of cis-Tramadol.

In a preferred embodiment of the invention the Mannich base is formed by forming a Mannich hydrochloride and liberating the Mannich base. Preferably, the Mannich hydrochloride is formed by reaction of cyclohexanone with paraformaldehyde and diethylamine hydrochloride to form dimethylaminomethyl-cyclohexanone hydrochloride. In one embodiment of the invention, the Mannich base is liberated by treating the Mannich hydrochloride with a base such as sodium hydroxide in a solvent system which may comprise a mixture of toluene, methyl t-butylether and water.

In a preferred embodiment of the invention, the cis-Tramadol hydrochloride is formed from the cis-Tramadol base hydrate by acidification with hydrochloric acid.

The invention also provides Tramadol and salts thereof whenever prepared by the process of the invention.

We have found that pure cis-2[(dimethylamino)methyl]-1-(3-dimethoxyphenyl) cyclohexanol forms very selectively with equimolar amount of water a monohydrate which solidifies in a crystalline form.

In comparison cis-Tramadol base in anhydrous form at room temperature is an oil. Surprisingly it was found that cis-Tramadol base monohydrate is a stable derivative, which can be crystallised very easily, purified and can be used to produce pure cis-Tramadol hydrochloride.

The base monohydrate of cis-Tramadol can also be formulated in different forms. The invention therefore includes therapeutical drugs, which can be used in human or veterinarian medicines. Such drugs can be formulated with the usual pharmaceuticals ingredients.

The base hydrate of cis-Tramadol can be formulated for oral, buccal, topical, parenteral or rectal use. For example, for the oral application the base monohydrate of cis-Tramadol can be formulated as tablets, in capsules, powder, in solution, as a syrup or in suspension, which can be stabilised and produced with emulsion of oily ingredients.

DETAILED DESCRIPTION OF THE INVENTION

The invention will be more clearly understood from the following description thereof given by way of example only.

In the improved process of the invention, the first step is the reaction of cyclohexanone with paraformaldehyde and dimethylamine hydrochloride to form the Mannich hydrochloride, dimethylaminomethylcyclohexanone hydrochloride, which is recovered from acetone.

The Mannich hydrochloride formed in Step 1 is treated with sodium hydroxide in a mixture of toluene, methyl t-butyl ether and water to liberate the Mannich base.

The Mannich base is then reacted with a Grignard reagent to form a crude cis-Tramadol base hydrate.

The cis-Tramadol base hydrate is then purified by recrystallisation from ethyl acetate.

Finally, cis-Tramadol hydrochloride is formed from the cis-Tramadol base hydrate by acidification with hydrochloric acid.

In general, the reaction scheme may be illustrated as follows.

In this scheme only the (RR)-enantiomer of the Tramadol Base Hydrate is illustrated. It will be appreciated that both the (RR) and (SS) enantiomers are present in the same way as cis-Tramadol as defined above.

Step 1 Formation of Dimethylaminomethyl Cyclohexanone Hydrochloride

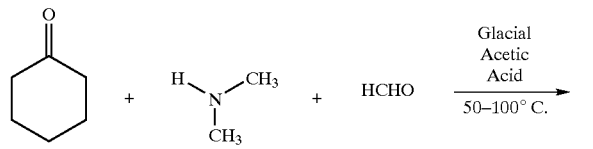

Step 2 Formation of Tramadol Mannich Base

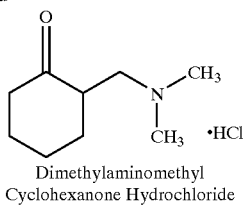

Dimethylaminomethyl Cyclohexanone Hydrochloride

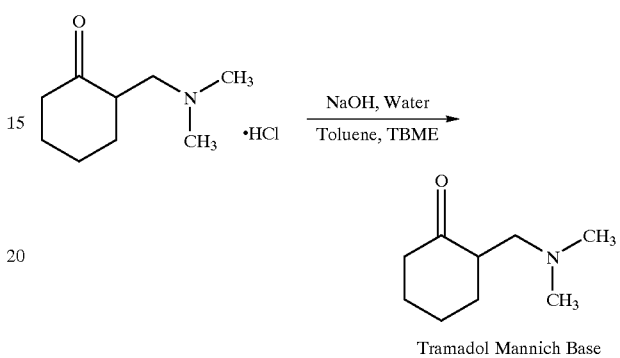

Tramadol Mannich Base

Step 3 Formation of Tramadol Base Hydrate

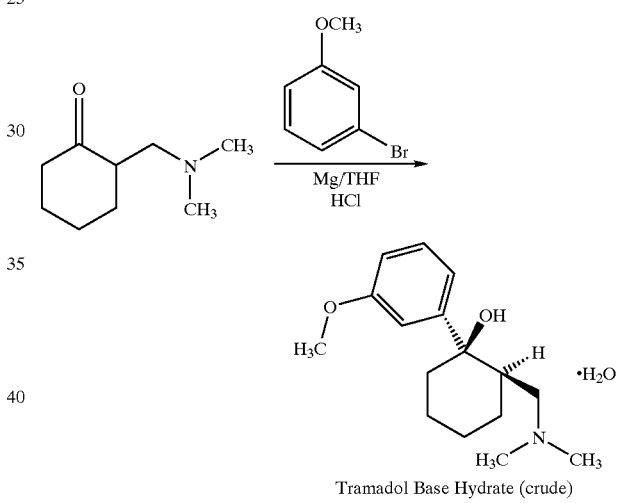

Tramadol Base Hydrate (crude)

Step 4 Purification of Tramadol Base Hydrate

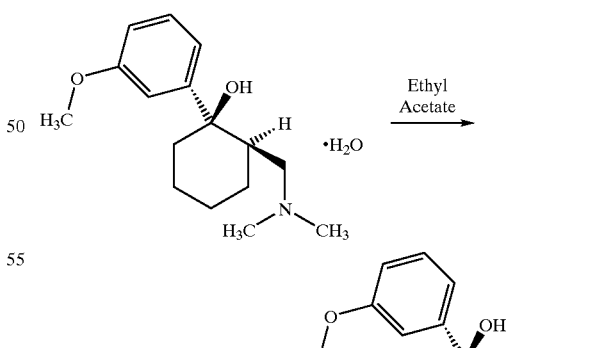

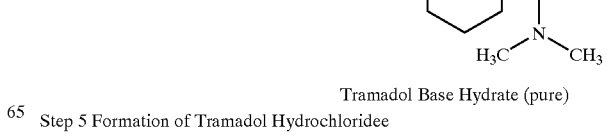

Tramadol Base Hydrate (pure)

Step 5 Formation of Tramadol Hydrochloridee

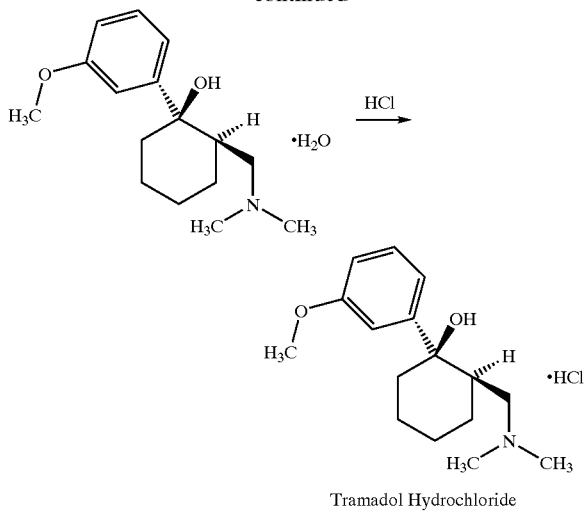

Tramadol Hydrochloride

EXAMPLE 1

To produce the Tramadol base hydrate, a reaction vessel is charged successively with 69 Kg of Magnesium, 400 l of dry Tetrahydrofuran (THF) and 15 l of 3-bromoanisole.

With careful heating, the reactor temperature is brought up to ca. 30° C. The Grignard initiates at this point and exotherms to approximately 50° C. A further 5 l of bromoanisole are added which maintains reflux. 400 l of THF are then added before the remainder of the bromoanisole. This addition of the remainder of the bromoanisole is carried out slowly so as to sustain a gentle reflux. The reaction is refluxed after complete addition of 3-bromoanisole. The vessel is cooled and Mannich base is added. When addition is complete, the vessel is reheated to reflux for 30 minutes to ensure complete reaction. After cooling to ca. 10° C., 2,300 l of water are added to quench the reaction. When complete, part of the solvents are distilled under vacuum. Approximately 260 l of concentrated HCl is added at a low temperature until a pH of 0–1 is reached. This aqueous phase is extracted with toluene. The toluene phases are discarded and ethyl acetate is added to the aqueous phase. 30% Ammonia solution is then charged to reach pH 9–10 and the phases are separated. The aqueous phases are extracted again with ethyl acetate and finally all ethyl acetate layers are combined and washed twice with water. Ethyl acetate is then distilled from the reaction solution at atmospheric pressure. Process water is added and the solution cooled to 200° C. and seeded. After crystallisation, the vessel is cooled to −5 to 0° C. and stirred for one hour.

The product is centriftged at this temperature and washed with cold ethyl acetate 5×50 l. Approximately 310–360 Kg of moist cis-Tramadol base hydrate are obtained.
Purification A reactor vessel is charged successively with cis-Tramadol base hydrate (crude) 200 Kg and ethyl acetate 300 l and the contents of the vessel heated to 50° l C. until all solids are in solution. The vessel is then cooled to −5 to 0° C. and the product crystallises. Stirring is continued for two hours and the product is then centrifuged and washed with cold ethyl acetate, 2×25 l. Approximately 165–175 Kg (moist) of cis(+/−) Tramadol base hydrate are obtained from this procedure.

The overall process produced high yields of cis-Tramadol with a trans isomer content of less than 0.03%.

Analytical data of the base hydrate of cis-Tramadol

Melting point: 79–80° C. (in comparison cis-Tramadol base anhydrous is an oil).

Water content (KF): 6.52% (=monohydrate)

IR-spectrum of the base hydrate of cis-Tramadol (see FIG. 1).

Figure 2:
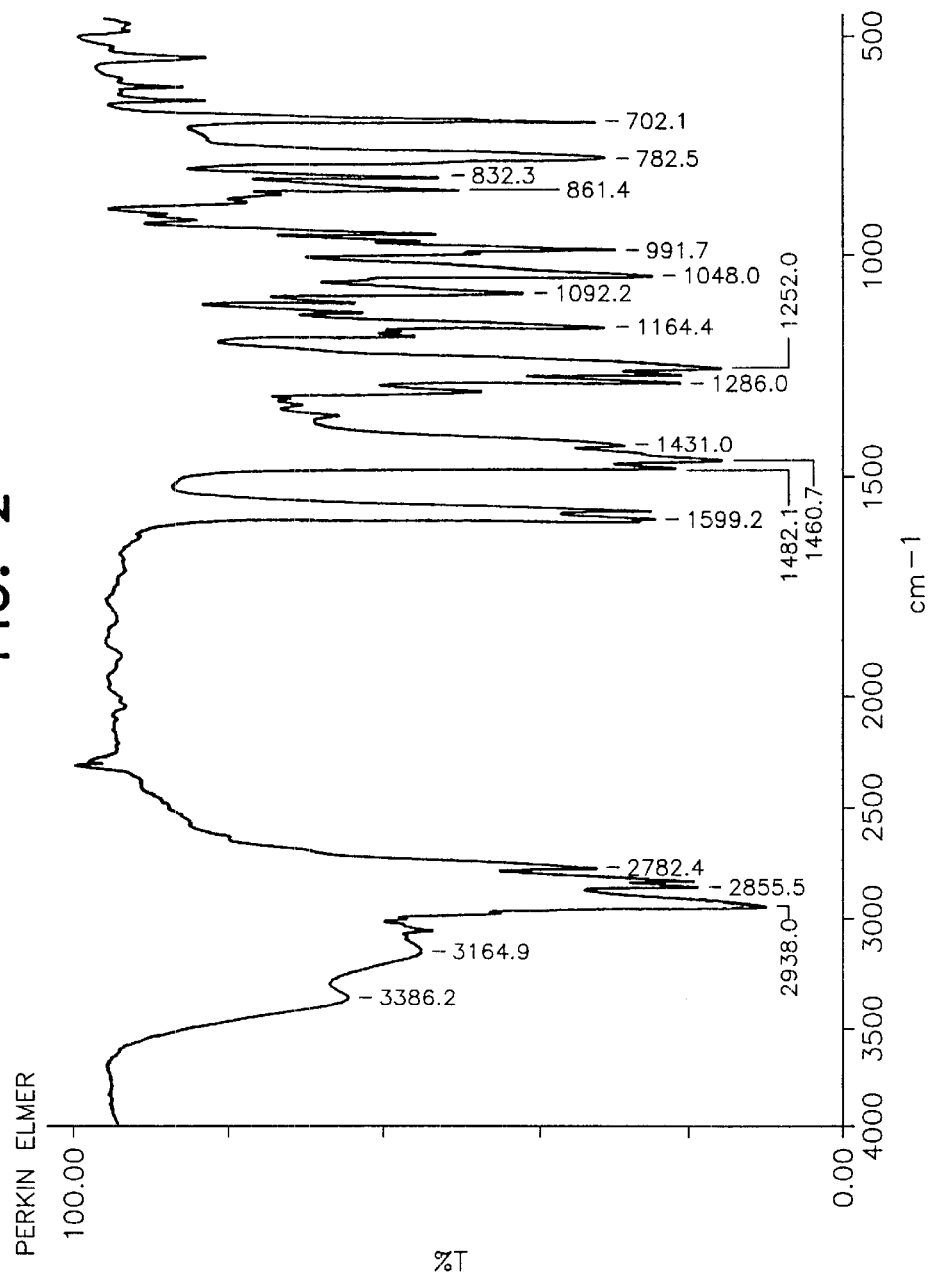

IR-spectrum (=cis-Tramadol base anhydrous, see FIG. 2).

The invention provides a unique process in which a base hydrate of cis-Tramadol is selectively crystallised without impurities. The base hydrate is processed to readily form cis-Tramadol hydrochloride. The process is substantially simpler than known processes and does not require the use of potentially toxic solvents. Thus the process is environmentally friendly.

The base hydrate of cis-Tramadol prepared may also be used in various formulations.

The base hydrate of cis-Tramadol may be formulated in the form of a solid with a slow release profile. For example, slow release pellets may be prepared by coating a suitable core material with a coating, for example, of ethylcellulose/schellack solution (4:1) and suitable pharmaceutical excipients. The pellets have typical average diameter of 0.6 to 1.6 mm. The pellets may be readily converted into gelatine capsules or pressed into tablet form using well-known techniques.

Alternatively the base hydrate of cis-Tramadol may be formulated into effervescent tablets by forming granules of the base hydrate with acidity/taste modifiers and a suitable effervescent base such as sodium hydrogen carbonate/anhydrous sodium carbonate (12:1). The ingredients are typically blended in a mixer/granulator and heated until granulation occurs. The resulting granules may be pressed into tablet form, on cooling.

Of particular interest is the use of the base hydrate of cis-Tramadol in a form for parenteral use/injectables. The base hydrate is typically dissolved in water together with suitable excipients (as necessary). The solution is filtered through a membrane to remove solid fibres or particles. The filtered solution may then be filled into ampoules, typically containing 10.0 mg of the active compound. Usually the formulation is prepared for intramuscular injection.

The invention is not limited to the embodiments hereinbefore described which may be varied in detail.

What is claimed is:

1. A process for preparing pure cis-Tramadol hydrochloride comprising the steps of:

reacting a Mannich base with a Grignard reagent to form the base hydrate of cis-Tramadol;

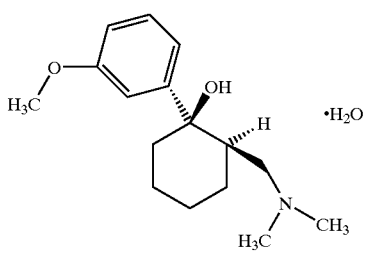

and
   forming cis-Tramadol hydrochloride from the base hydrate of cis-Tramadol.

2. A process as claimed in claim 1 wherein the Tramadol hydrochloride is formed from the base hydrate of cis-Tramadol by acidification with hydrochloric acid.

3. A process as claimed in claim 1 wherein the Mannich base is formed by:
   forming a Mannich hydrochloride; and
   liberating the Mannich base.

4. A process as claimed in claim 3 wherein the Mannich hydrochloride is formed by reaction of cyclohexanone with paraformaldehyde and diethylamine hydrochloride to form dimethylaminomethylcyclohexanone hydrochloride.

5. A process as claimed in claim 3 wherein the Mannich base is liberated by treating the Mannich hydrochloride with a base in a solvent system.

6. A process for preparing Tramadol hydrochloride comprising using a base hydrate of cis-Tramadol as an intermediate.

7. The process as claimed in claim 1 wherein the Grignard reagent is the Grignard reagent of 3-bromoanisole.

8. The process as claimed in claim 1 wherein the Mannich base is dimethylaminomethyl cyclohexanone.

9. The process as claimed in claim 1 wherein the Mannich hydrochloride is dimethylaminomethyl cyclohexanone hydrochloride.

10. A process for preparing pure cis-Tramadol hydrochloride comprising, as sole essential reaction steps:
   a) forming Tramadol Mannich Base,
   b) forming cis-Tramadol Base Hydrate from the Tramadol Mannich Base, and
   c) forming cis-Tramadol Hydrochloride from the cis-Tramadol Base Hydrate.

11. A process as claimed in claim 5 wherein the base is sodium hydroxide.

12. A process as claimed in claim 5 wherein the solvent system comprises a mixture of toluene, methyl t-butylether and water.

* * * * *